United States Patent [19]

Takeuchi et al.

[11] Patent Number: 5,563,276

[45] Date of Patent: Oct. 8, 1996

[54] POLYMERIZATION OF ACRYLIC ACID AND DERIVATIVES THEREOF USING AZOAMIDOXIME SALT

[75] Inventors: Hideo Takeuchi; Toshiyasu Ito, both of Kawagoe; Yutaka Kojima, Ako, all of Japan

[73] Assignee: Waco Pure Chemical Industries, Ltd., Osaka, Japan

[21] Appl. No.: 423,754

[22] Filed: Apr. 18, 1995

[30] Foreign Application Priority Data

Apr. 25, 1994 [JP] Japan .................... 6-109006
Aug. 22, 1994 [JP] Japan .................... 6-219416

[51] Int. Cl.$^6$ .............. C08F 4/04; C07C 245/02; C07C 245/04
[52] U.S. Cl. .............. 526/219; 526/303.1; 526/317.1; 534/573; 534/838; 534/850; 534/886
[58] Field of Search .............. 534/838, 886, 534/850, 573 M; 526/219, 303.1, 317.1

[56] References Cited

U.S. PATENT DOCUMENTS

| | | | |
|---|---|---|---|
| 2,599,299 | 6/1952 | Upson | 534/838 |
| 2,744,105 | 5/1956 | Barney | 534/838 X |
| 4,528,347 | 7/1985 | Harada et al. | 526/219 |
| 4,644,042 | 2/1987 | Ueda et al. | 526/204 |
| 4,916,216 | 4/1990 | Tanaka et al. | 534/738 |

FOREIGN PATENT DOCUMENTS

| | | | |
|---|---|---|---|
| 0196588A2 | 8/1986 | European Pat. Off. | 526/204 |
| 2602512 | 12/1988 | France | 526/219 |
| 57-131751 | 8/1982 | Japan | 534/838 |
| 61-60707 | 3/1986 | Japan | 526/219 |
| 61-223009 | 10/1986 | Japan | 526/219 |
| 62-172007 | 7/1987 | Japan | 526/219 |
| 64-26545 | 1/1989 | Japan | 534/838 |
| 2111979 | 7/1983 | United Kingdom | 534/838 |

OTHER PUBLICATIONS

Derwent Publication—SU–A 891695—Abstract (1986).
Derwent Publication—SU–A 718461—Abstract (1985).
Derwent Publication—SU–A 487087—Abstract (1984).
Derwent Publication—SU–A 301329—Abstract (1980).
Pol 104,742 (C.A. 95:80213w) Abstract only (1981).
Can. J. Chem. vol. 65, pp. 2541–2550 (1987) Barclay et al.
Chem. Abstr. vol. 107 (1987), 107:217956d Abstract only.

*Primary Examiner*—Floyd D. Higel
*Attorney, Agent, or Firm*—Armstrong, Westerman, Hattori, McLeland & Naughton

[57] ABSTRACT

Acrylic acid or water-soluble derivatives thereof can be polymerized effectively in a short time using as a polymerization initiator an inorganic acid salt or organic acid salt of 2,2'-azobis(2-methylpropionamidoxime).

11 Claims, 3 Drawing Sheets

5,563,276

POLYMERIZATION OF ACRYLIC ACID AND DERIVATIVES THEREOF USING AZOAMIDOXIME SALT

BACKGROUND OF THE INVENTION

This invention relates to a process for producing a polymer or copolymer of acrylic acid or a water-soluble derivative thereof. More in detail, the present invention relates to a process for producing a polymer or copolymer of acrylic acid or a water-soluble derivative thereof using a special polymerization initiator in a short time with high efficiency.

Water-soluble vinyl polymers and copolymers such as poly(acrylic acid) or salts thereof, polyacrylamide, polyvinylpyrrolidone, and the like have been noticed for their utilities. For example, polyacrylates and copolyacrylates are widely used, for example, as a thickener, a flocculant, a highly water-absorbing resin which is used in large amounts for disposal diaper, etc. Acrylamide polymers are widely used, for example, as a flocculant, a thickener, a yield improving agent for paper-making, a fluidity adjusting agent for oil salvage, etc. Such water-soluble polymers and copolymers used for such purposes have been obtained by polymerizing or copolymerizing acrylic acid, acrylamide, or derivatives thereof as a monomer or monomers in an aqueous solution or a suspension of water and water-insoluble organic solvent using a redox polymerization initiator which is a combination of an oxidizing agent (e.g. a peroxide) and a reducing agent, a peroxide polymerization initiator such as benzoyl peroxide, lauroyl peroxide, potassium persulfate, etc. an azo polymerization initiator such as 2,2'-azobis(2-amidinopropane) dihydrochloride,etc.

But these known polymerization processes have various problems therein. For example, in the case of using the redox polymerization initiator and the peroxide polymerization initiator, since peroxides per se used therein are generally unstable for impact, heating, etc., there is a danger of fire, explosion, and the like during the storage of the peroxides or at the time of polymerization. Further, many problems also arise when applied to industrial production, for example, a long time being necessary for polymerization due to a long induction period, the temperature control at the time of reaction being difficult due to easy self-induced decomposition, and the like. In addition, according to the polymerization process using such polymerization initiators, since the polymer obtained has a small molecular weight, there is a problem of failing to obtain a sufficient aggregating effect when used as a flocculant.

On the other hand, in a process using an azo polymerization initiator such as 2,2'-azobis(2-amidinopropane) dihydrochloride, there is a merit of easy temperature control due to precise primary decomposition, not showing self-induced decomposition unlike the peroxides, but-there is also a problem of easily bringing about the so-called dead-end phenomenon wherein the polymerization is stopped due to consumption of the polymerization initiator during the polymerization under preferable polymerization conditions.

As azo polymerization initiators, the use of 2,2'-azobis(2-methylpropionamidoxime) is disclosed, for example, in Japanese Patent Unexamined Publication (JP-A) Nos. 62-172007, and 61-223009 (E.P 196588), U.S. Pat. Nos. 4,528,347, and 4,644,042 (=JP-A 61-60707) for polymerization of monoallylamine ($CH_2=CHCH_2NH_2$) which is a basic allyl compound and in U.S.S.R. SU 927,802 for polymerization of acrylonitrile, which is not water-soluble. No prior art reference discloses the use of such an azo initiator for polymerization of acidic or neutral water-soluble vinyl compounds such as acrylic acid, acrylamide, etc.

SUMMARY OF THE INVENTION

It is an object of the present invention to provide a process for producing a polymer or copolymer of acrylic acid or a water-soluble derivative thereof efficiently in a short time overcoming the problems of the redox polymerization initiators and peroxide polymerization initiators which cause a danger of explosion, self-induced decomposition at the time of polymerization, and also overcoming the problems of the dead-end phenomenon caused by the use of azo polymerization initiators such as 2,2'-azobis(2-amidinopropane) dihydrochloride, etc. It is another object of the present invention to provide a water-soluble polymerization initiator used therein.

The present invention provides a process for producing a polymer or copolymer of acrylic acid or a water-soluble derivative thereof, which comprises polymerizing acrylic acid or a water-soluble derivative thereof using as a polymerization initiator an inorganic acid salt or an organic acid salt or a mixture of inorganic acid salt and organic acid salt of 2,2'-azobis( 2-methylpropionamidoxime).

The present invention also provides an inorganic or organic acid salt of 2,2'-azobis(2-methylpropionamidoxime) obtained by reacting 2,2'-azobis(2-methylpropionamidoxime) with an acid having a pKa of 4.25 or less at 25° C.

DESCRIPTION OF THE PREFERRED EMBODIMENTS

Figure 1:
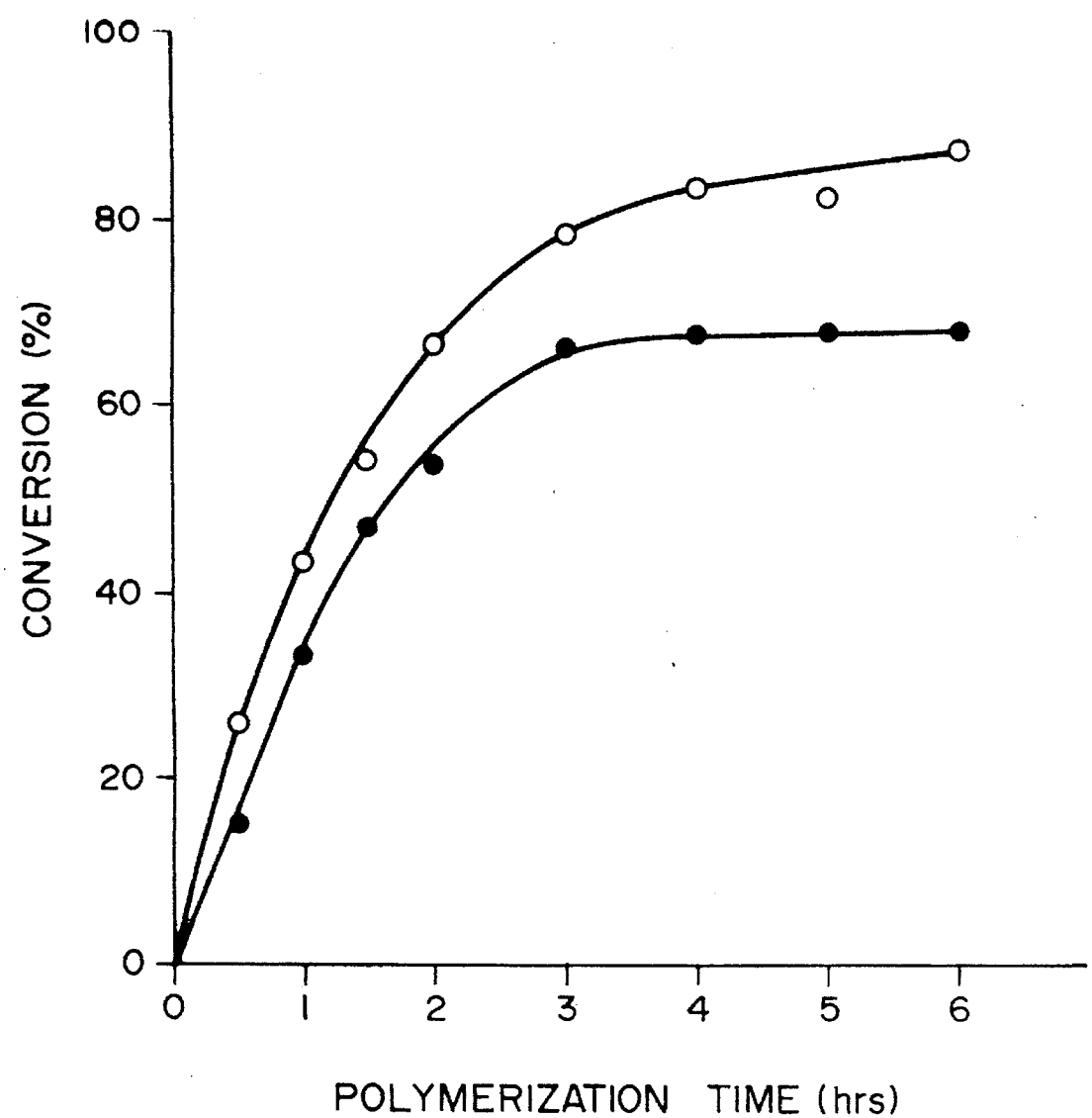
FIG. 1 is a graph showing conversion-polymerization time curves obtained in Example 1 and Comparative Example 3.

The present inventors studied polymerization initiators for obtaining polymers and copolymers of acrylic acid and water-soluble derivatives thereof effectively in a short time using an azo polymerization initiator which is slight in danger of explosion and hardly causes self-induced decomposition during the polymerization, and is free from the dead-end phenomenon in contrast to the use of 2,2'-azobis(2-amidinopropane) dihydrochloride, and accomplished the present invention.

The polymerization initiator used in the present invention is an inorganic or organic acid salt of 2,2'-azobis(2-methylpropionamidoxime).

It is possible to obtain 2,2'-azobis(2-methylpropionamidoxime) for example, by reacting azobisisobutyronitrile (AIBN) with hydroxylamine in water (disclosed in U.S.S.R. Pat. No. 301329), or reacting AIBN with hydroxylamine in ethanol as a solvent (Polish Patent No. 104742). Further, 2,2'-azobis(2-methylpropionamidoxime) can be produced by reacting AIBN with hydroxylamine in an amount of 1 to 3 equivalent in dimethylsulfoxide (DMSO), N-methyl-2-pyrrolidone (NMP), or a solvent containing DMSO or NMP as a major component at 20° to 40° C. for 4 to 8 hours (developed by the present inventors).

Inorganic or organic acid salts of 2,2'-azobis( 2-methylpropionamidoxime) can be produced by reacting 2,2'-azobis(2-methylpropionamidoxime) with an inorganic acid or organic acid (preferably having a pKa of 4.25 or less at 25° C.) in an amount of 1 to 3 equivalent in a solvent such as a lower alcohol, e.g. methanol, ethanol, isopropanol, etc., or water, at 10° to 40° C. for about 1 to 10 hours. When the acid does not have a pKa of 4.25 or less at 25° C. (e.g. acetic acid), it is impossible to obtained the desired salt of 2,2'-azobis( 2-methylpropionamidoxime).

As the inorganic acid, there can be used hydrochloric acid, sulfuric acid, phosphoric acid, etc. As the organic acid, there can be used organic sulfonic acids such as methanesulfonic acid, p-toluenesulfonic acid, etc.; carboxylic acids such as trifluoroacetic acid, oxalic acid, succinic acid, citric acid, tartaric acid, malic acid, glycolic acid, malonic acid, etc. These acids can be used singly or as a mixture thereof.

In some cases, the inorganic or organic acid salt of 2,2'-azobis(2-methylpropionamidoxime) can be replaced by a mixture of 2,2'-azobis(2-methylpropionamidoxime) and an acid in an aqueous solution. As the acid, there is no particular limitation so long as an acid has a function for enhancing water-solubility of 2,2'-azobis(2-methylpropionamidoxime). Preferable examples of the acid are inorganic acids such as hydrochloric acid, sulfuric acid, phosphoric acid, etc.; organic sulfonic acids such as methanesulfonic acid, p-toluenesulfonic acid, etc.; carboxylic acids such as acetic acid, trifluoroacetic acid, oxalic acid, succinic acid, citric acid, tartaric acid, malic acid, glycolic acid, malonic acid, etc. These acids can be used singly or as a mixture thereof. By adding an acid (preferably in an amount of 0.5 to 50, more preferably 1 to 20 equivalent) to 2,2'-azobis(2-methylpropionamidoxime) in the polymerization system, it seems to cause the same effects as the case of using the inorganic or organic acid salt of 2,2'-azobis(2-methylpropionamidoxime). When monomer or monomers to be polymerized show acidity by themselves, e.g. acrylic acid, methacrylic acid, 2-acrylamide-2-methylpropanesulfonic acid, etc., it is not necessary to add an acid to the reaction system.

As the monomer to be polymerized, there can be used acrylic acid and water-soluble derivatives thereof such as acrylamide, methacrylamide, N-methylolacrylamide, N-methylolmethacrylamide, methacrylic acid, 2-acrylamide-2-methylpropanesulfonic acid, and salts thereof e.g. alkali metal (Na, K, Li) or ammonium salts thereof; dimethylaminoethyl acrylate, dimethylaminoethyl methacrylate, N,N-dimethylaminopropylacrylamide, N,N-dimethylaminopropylmethacrylamide, or acid addition salts thereof wherein the acid is an inorganic acid such as HCl, $H_2SO_4$, etc., or an organic acid such as acetic acid, p-toluenesulfonic acid, etc, or quaternary salts thereof. These monomers can be used singly (to obtain homopolymers) or as a mixture thereof (to obtain copolymers). Among these monomers, the use of acrylic acid, methacrylic acid, acrylamide, and methacrylamide, is preferable.

It is possible to use one or more comonomers which can be copolymerizable with the monomers mentioned above, for example, N,N'-methylenebisacrylamide, N,N'-methylenebismethacrylamide, trimethylolpropane diallyl ether, trimethylolpropane diacrylate, and oil-soluble monomers such as styrene, methyl methacrylate, etc. in amounts not to give undesirable influences to the copolymerization.

The concentration of the monomer such as acrylic acid or a water-soluble derivative thereof in the polymerization solution is not particularly limited so long as there is no trouble in the polymerization. From the viewpoint of exothermic heat at the time of polymerization and temperature control thereof and economy at the time of isolation of the obtained polymer, the concentration of 5 to 80% by weight/weight (w/w) is preferable and 10 to 50% by w/w is more preferable.

The amount of the polymerization initiator is sufficient when the polymerization can be carried out desirably (i.e. the catalytic amount). Too low amount is undesirable due to too slow polymerization. On the other hand, too much amount is undesirable for lowering the conversion or making the temperature control difficult. Usually the inorganic or organic acid salt of 2,2'-azobis(2-methylpropionamidoxime) is used in an amount of 0.001 to 5% by weight, preferably 0.01 to 2% by weight, based on the weight of the monomer or monomers.

The polymerization can be carried out at a temperature below the boiling point of water, usually at 30° to 80° C., preferably 50° to 70° C., for 3 to 10 hours. The polymerization time can be changed depending on reaction conditions such as the polymerization temperature, the kind of monomer or monomers to be polymerized, the concentration of polymerization initiator, etc.

As the polymerization method, there can preferably be used reverse-phase suspension polymerization, aqueous solution polymerization, etc.

For example, the polymerization can be carried out by placing a monomer or monomers (e.g. acrylic acid, a water-soluble derivative thereof, and if necessary, other comonomer or comonomers) in a solvent (e.g. water, a mixed solvent of water and a water-soluble organic solvent), and polymerizing the monomer or monomers in the presence of a catalytic amount of an inorganic or organic acid salt of 2,2'-azobis(2-methylpropionamidoxime), or a mixture of a catalytic amount of 2,2'-azobis( 2-methylpropionamidoxime) and an acid in a nitrogen stream according to a conventional process. As the water-soluble organic solvent, there can be used water-soluble alcohols such as methanol, ethanol, etc.; water-soluble cyclic ethers such as tetrahydrofuran (THF), dioxane, etc.; acetone, dimethylsulfoxide (DMSO), etc.

The obtained polymer or copolymer can be isolated by a conventional process.

The present invention is illustrated by way of the following Examples.

Reference Example 1

To 100 ml of dimethylsulfoxide (DMSO), 32.8 g of azobisisobutyronitrile (AIBN) and 31.7 g of aqueous solution of 50% hydroxylamine were added and reacted at 30° C. for 8 hours with stirring. After allowed to stand overnight, 115 ml of water was added to the reaction solution. Deposited crystals were filtered, washed with water and then methanol and dried to give 44.6 g of white 2,2'-azobis(2-methylpropionamidoxime) (yield 97.0%). The obtained 2,2'-azobis(2-methylpropionamidoxime) was subjected to analysis using high performance liquid chromatography (HPLC) [apparatus: 600 type, mfd. by Waters Co., Ltd.; column: Wakosil, a trade name, mfd. by Wako Pure Chemical Industries, Ltd., 5C18 4.6 mm in diameter and 150 mm long; eluent: tetra-n-butylammonium hydroxide 0.005M, sodium 1-octanesulfonate 0.005M, pure water 860 ml and acetonitrile 140 ml were mixed, and dissolved, followed by adjustment of pH to 4.00 using phosphoric acid; flow rate of eluent: 1.0 ml/min]. The content of 2,2'-azobis(2-methylpropionamidoxime) was 99.1%.

Reference Example 2

The process of Reference Example 1 was repeated in the same manner as described in Reference Example 1 except for using 100 ml of N-methyl-2-pyrrolidone (NMP) in place of DMSO to give 43.4 g of 2,2'-azobis(2-methylpropionamidoxime) (yield 94.4%). After subjected to analysis using HPLC in the same manner as described in Reference Example 1, the content of 2,2'-azobis(2-methylpropionamidoxime) was 98.1%.

Synthesis Example 1

Synthesis of 2,2'-azobis(2-methylpropionamidoxime) dihydrochloride

To 450 ml of methanol, 90.1 g of 2,2'-azobis( 2-methylpropionamidoxime) was added, followed by addition of a solution obtained by dissolving 37.2 g of hydrogen chloride gas in 50 ml of methanol to carry out the reaction at room temperature for 2 hours with stirring. After the reaction, the methanol was removed by distillation. The residue was purified with water-acetone to give 104.2 g of 2,2'-azobis(2-methylpropionamidoxime) dihydrochloride (yield 87.8%), having a melting point (m.p.) of 139° C. (decomposed).

IR (KBr) vcm$^{-1}$: 1660 (C=N—) $^1$HNMR δppm (D$_2$O): 1.46 (12H, s, C$\underline{H}_3$) UV (H$_2$O): λmax 365 nm (ε=23.8)

Synthesis Example 2

Synthesis of 2,2'-azobis(2-methylpropionamidoxime) disuccinate

To 50 ml of ethanol, 4.7 g of succinic acid [pKa=4.207 (pK$_1$) (25° C.)] and 2.3 g of 2,2'-azobis(2-methylpropionamidoxime) were added and reacted at 30° C. for 3.5 hours. After the reaction, deposited crystals were filtered, washed with 10 ml of ethanol and dried to give 3.46 g of 2,2'-azobis(2-methylpropionamidoxime) disuccinate (yield 74.3%) having a m.p. of 126.5° C. (decomposed).

IR (KBr) vcm$^{-1}$: 1710 (C=O), 1640 (C=N—) $^1$HNMR δppm (D$_2$O): 1.47 (12H, s, C$\underline{H}_3$), 2.59 (8H, s, C$\underline{H}_2$) UV (H$_2$O): λmax 365 nm (ε=26.6)

Synthesis Example 3

Synthesis of 2,2'-azobis(2-methylpropionamidoxime) dicitrate

To 60 ml of isopropanol, 7.7 g of citric acid [pKa=3.128 (pK$_1$) (25° C.)] and 2.3 g of 2,2'-azobis(2-methylpropionamidoxime) were added and reacted at 25° C. for 6.5 hours with stirring. After the reaction, deposited crystals were filtered, washed with 10 ml of ethanol, and dried to give 5.43 g of 2,2'-azobis(2-methylpropionamidoxime) dicitrate (yield 88%) having a m.p. of 122.5° C. (decomposed).

IR (KBr) vcm$^{-1}$: 1720 (C=O), 1640 (C=N—) $^1$HNMR δppm (D$_2$O): 1.52 (12H, s, $\underline{H}_3$), 2.75–2.95 (8H, d×2, C$\underline{H}_2$) UV (H$_2$O): λmax 365 nm (ε=26.7)

Synthesis Example 4

Synthesis of 2,2'-azobis(2-methylpropionamidoxime) dioxalate

To 30 ml of methanol, 2 g of oxalic acid [pKa=1.271 (25° C.)] and 2.3 g of 2,2'-azobis(2-methylpropionamidoxime) were added and reacted at 30° C. for 1.5 hours with stirring. After the reaction, deposited crystals were filtered, washed with 10 ml of methanol, and dried to give 3.75 g of 2,2'-azobis(2-methylpropionamidoxime) dioxalate (yield 91.5%) having a m.p. of 146.5° C. (decomposed).

IR (KBr) vcm$^{-1}$: 1700 (C=O), 1625 (C=N—) $^1$HNMR δppm (D$_2$O): 1.53 (12H, s, C$\underline{H}_3$) UV (H$_2$O): λmax 366 nm (ε=23.9)

Synthesis Example 5

Synthesis of 2,2'-azobis(2-methylpropionamidoxime) monotartarate

To 50 ml of ethanol, 6.0 g of tartaric acid [pKa=3.831 (pK$_1$) (25° C.)] and 2.3 g of 2,2'-azobis(2-methylpropionamidoxime) were added and reacted at 30° C. for 5 hours with stirring. After the reaction, deposited crystals were filtered, washed with 10 ml of ethanol, and dried to give 2.96 g 2,2'-azobis(2-methylpropionamidoxime) monotartarate (yield 77.9%) having a m.p. of 112° C. (decomposed).

IR (KBr) vcm$^{-1}$: 1710 (C=O), 1660 (C=N—) $^1$HNMR δppm (D$_2$O ): 1.49 (12H, s, C$\underline{H}$hd 3), 4.45 (2H, s, C$\underline{H}$) UV (H$_2$O): λmax 365 nm (ε=27.6)

Synthesis Example 6

Synthesis of 2,2'-azobis(2-methylpropionamidoxime) dimalate

To 50 ml of ethanol, 5.36 g of malic acid [pKa =3.40 (pK$_1$) (25° C.)] and 2.3 g of 2,2'-azobis(2-methylpropionamidoxime) were added and reacted at 30° C. for 4 hours with stirring. After the reaction, deposited crystals were filtered, washed with 10 ml of ethanol and dried to give 4.21 g of 2,2'-azobis(2-methylpropionamidoxime) dimalate (yield 84.6%) having a m.p. of 116° C. (decomposed).

IR (KBr) vcm$^{-1}$: 1710 (C=O), 1650 (C=N—) $^1$HNMR δppm (D$_2$O): 1.50 (12H, s, C$\underline{H}_3$), 2.65–2.89 (4H, m, C$\underline{H}_2$), 4.41–4.46 (2H, m, C$\underline{H}$) UV (H$_2$O): λmax 365 nm (ε=27.6)

Synthesis Example 7

Synthesis of 2,2'-azobis(2-methylpropionamidoxime) di-p-toluenesulfonate

To 100 ml of ethanol, 19 g of p-toluenesulfonic acid [pKa=1.7 (25° C.)] and 11.5 g of 2,2'-azobis( 2-methylpropionamidoxime) were added and reacted at 25° C. for 3 hours with stirring. After the reaction, the ethanol was removed by distillation under reduced pressure. The residue was washed with 300 ml of acetone and dried to give 26.8 g of 2,2'-azobis(2-methylpropionamidoxime) di-p-toluenesulfonate (yield 93.2%) having a m.p. of 130° C. (decomposed).

IR (KBr) vcm$^{-1}$: 1210 (—SO$_3$H), 1460 (C$_6$H$_4$), 1670 (C=N—) $^1$HNMR δppm (D$_2$O): 1.41 (12H, s, C$\underline{H}_3$), 2.27 (6H, s, φ—C$\underline{H}_3$), 7.11 (4H, d, Ar—H(o-)), 7.49 (4H, d, Ar—H(m-)) UV (H$_2$O): λmax 365 nm (ε=23.7)

Synthesis Example 8

Synthesis of 2,2'-azobis(2-methylpropionamidoxime) dimethanesulfonate

To 125 ml of ethanol, 9.6 g (0.1 mole) of methanesulfonic acid and 11.5 g (0.05 mole) of 2,2'-azobis(2-methylpropionamidoxime) were added and reacted at 20°–25° C. for 4 hours with stirring. After the reaction, deposited crystals were filtered, washed with ethanol, and then acetone, and dried under reduced pressure to give 19.4 g of white 2,2'-azobis(2-methylpropionamidoxime) dimethanesulfonate (yield 91.8%) having a m.p. of 135° C. (decomposed).

IR (KBr) vcm$^{-1}$: 1709 (C=O), 1647 (C=N—) $^1$HNMR δppm (D$_2$O): 1.55 (12H, s, C—C$\underline{H}_3$), 2.49 (6H, s, S—C$\underline{H}_3$) UV (H$_2$O): λmax 365 nm (ε=24.1)

Synthesis Example 9

Synthesis of 2,2'-azobis(2-methylpropionamidoxime) diglycolate

To 125 ml of ethanol, 7.6 g (0.1 mole) of glycolic acid [pKa=3,831 (25° C.)] and 11.5 g (0.05 mole) of 2,2'-azobis(2-methylpropionamidoxime) were added and reacted at 20° C. for 4 hours with stirring. After the reaction, deposited crystals were filtered, washed with ethanol, and then acetone, and dried under reduced pressure to give 16.6 g of white 2,2'-azobis(2-methylpropionamidoxime) diglycolate (yield 86.8%) having a m.p. of 125° C. (decomposed).

IR (KBr) vcm$^{-1}$: 1716 (C=O), 1664 (C=N—) $^1$HNMR δppm (D$_2$O): 1.34 (12H, s, C$\underline{H}_3$), 3.99 (4H, s, C$\underline{H}_2$) UV (H$_2$O): λmax 365 nm (ε=31.1)

Comparative Examples 1 and 2

To 125 ml of ethanol, 6.0 g (0.1 mole) of acetic acid [pKa=4,756 (25° C.)] or 7.2 g (0.1 mole) of acrylic acid [pKa=4.26 (25° C.)] and 11.5 g (0.05 mole) of 2,2'-azobis(2-methylpropionamidoxime) were added and reacted at 20° C. for 4 hours with stirring. After the reaction, the same after-treatment as in Synthesis Examples 1 to 9 was carried out to give white powders. In any cases, the obtained compound was 2,2'-azobis(2-methylpropionamidoxime) (free form), and a salt of 2,2'-azobis(2-methylpropionamidoxime) was not isolated.

EXAMPLE 1

To 380 g of deionized water, 20 g of acrylamide and 0.01 g of 2,2'-azobis(2-methylpropionamidoxime) dihydrochloride were added and polymerized at 50° C. in a nitrogen atmosphere.

The results are shown in Table 1.

In FIG. 1, the results of Table 1 shown by a conversion-polymerization time curve (—○—).

Comparative Example 3

The process of Example 1 was repeated except for using 0.01 g of 2,2'-azobis(2-amidinopropane) dichloride (V-50, a trade name, mfd. by Wako Pure Chemical Industries, Ltd.) in place of 2,2'-azobis(2-methylpropionamidoxime) dihydrochloride.

The results are shown in Table 1.

In FIG. 1, the results of Table 1 are shown by a conversion-polymerization time curve (—●—).

TABLE 1

| | Polymerization time (hrs) | | | | | | | |
|---|---|---|---|---|---|---|---|---|
| | 0.5 | 1.0 | 1.5 | 2.0 | 3.0 | 4.0 | 5.0 | 6.0 |
| Example 1 | 26.0 | 43.5 | 54.4 | 66.7 | 78.5 | 83.5 | 82.7 | 87.6 |
| Comparative Example 3 | 14.9 | 33.3 | 47.4 | 53.8 | 66.2 | 67.9 | 68.1 | 68.0 |

In Table 1, values are conversion (%) per unit time.

As is clear from the results of Table 1 and FIG. 1, when V-50 is used as the polymerization initiator, the phenomenon of dead-end (i.e. saturation of polymerization) is observed after about 3 hours from the beginning of polymerization. In contrast, according to the process of the present invention, no dead-end phenomenon takes place and acrylamide can be polymerized effectively in a short time.

EXAMPLE 2

To 380 g of deionized water, 20 g of acrylamide, 0.01 g of 2,2'-azobis(2-methylpropionamidoxime) and 0.0052 g of acetic acid were added and polymerized at 50° C. in a nitrogen atmosphere.

The results are shown in Table 2.

Figure 2:
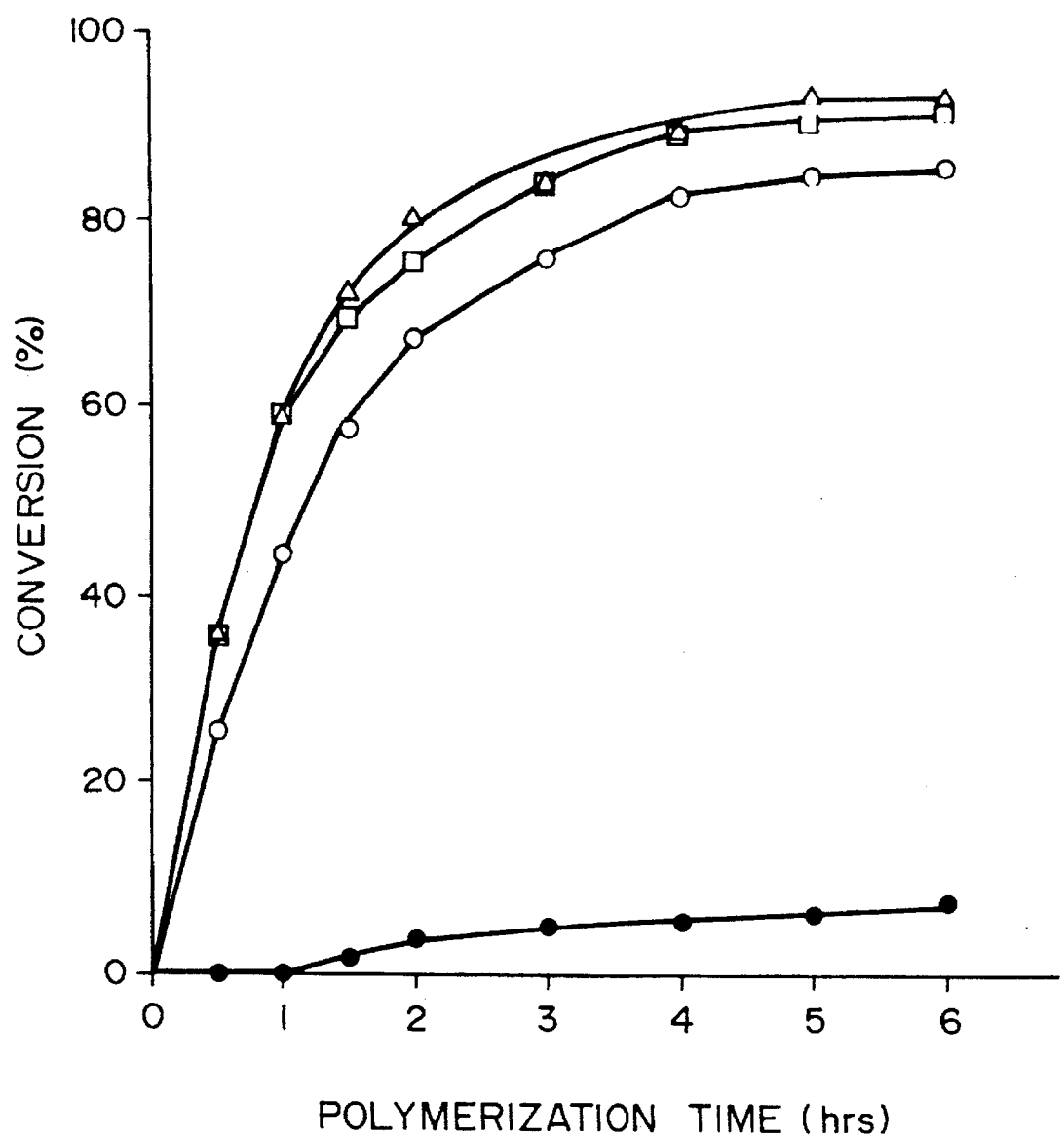
FIG. 2 is a graph showing conversion-polymerization time curves obtained in Examples 2, 3 and 4, and Comparative Example 4.

In FIG. 2, the results of Table 2 are shown by a conversion-polymerization time curve (—○—).

EXAMPLE 3

The process of Example 2 was repeated except for using 0.05 g of acetic acid in place of 0.0052 g of acetic acid.

The results are shown in Table 2.

In FIG. 2, the results of Table 2 are shown by a conversion-polymerization time curve (—△—).

EXAMPLE 4

The process of Example 2 was repeated except for using 0.0052 g of sulfuric acid in place of acetic acid.

The results are shown in Table 2.

In FIG. 2, the results of Table 2 are shown by a conversion-polymerization time curve (—□—).

Comparative Example 4

The process of Example 2 was repeated except for not using acetic acid.

The results are shown in Table 2.

In FIG. 2, the results of Table 2 are shown by a conversion-polymerization time curve (—●—).

TABLE 2

| | Polymerization time (hrs) | | | | | | | |
|---|---|---|---|---|---|---|---|---|
| | 0.5 | 1.0 | 1.5 | 2.0 | 3.0 | 4.0 | 5.0 | 6.0 |
| Example 2 | 25.8 | 44.7 | 57.9 | 67.5 | 75.8 | 82.4 | 84.6 | 85.4 |
| Example 3 | 36.4 | 59.4 | 72.2 | 80.4 | 83.8 | 89.4 | 93.3 | 93.1 |
| Example 4 | 36.1 | 59.3 | 69.5 | 75.6 | 83.9 | 88.9 | 90.2 | 91.4 |
| Comparative Example 4 | 0 | 0 | 1.9 | 3.8 | 5.2 | 5.8 | 6.5 | 7.8 |

In Table 2, values are conversion (%) per unit time.

As is clear from the results of Table 2 and FIG. 2, when 2,2'-azobis(2-methylpropionamidoxime) is used together with an acid, acrylamide can be polymerized effectively in a short time as in the case of Example 1.

EXAMPLE 5

To 360 g of deionized water, 40 g of acrylic acid and 0.0085 g ($3.7 \times 10^{-5}$ mole) of 2,2'-azobis(2-methylpropionamidoxime) were added and polymerized at 50° C. in a nitrogen atmosphere.

The results are shown in Table 3.

Figure 3:
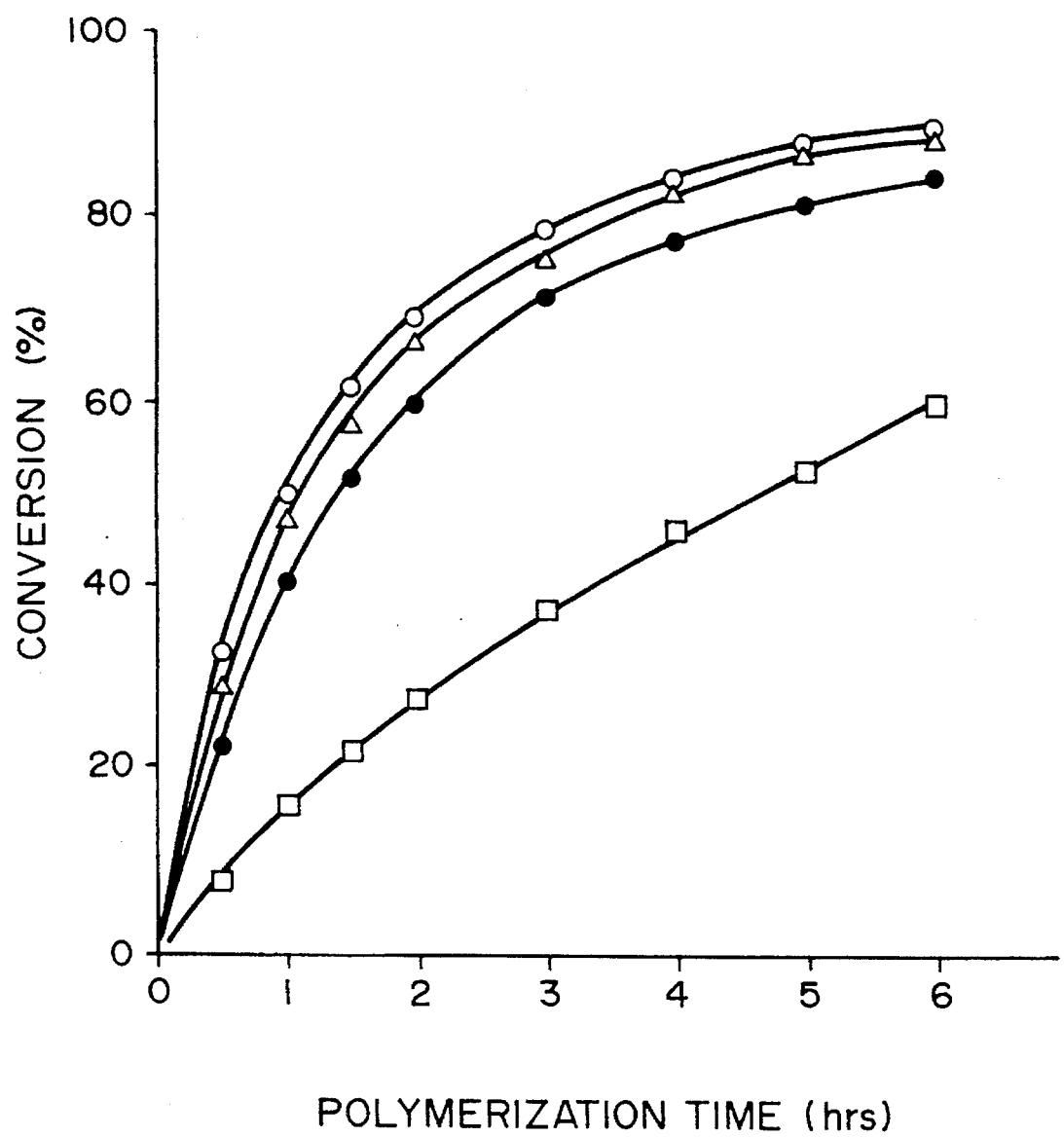
FIG. 3 is a graph showing conversion-polymerization time curves obtained in Examples 5 and 6, and Comparative Examples 5 and 6.

In FIG. 3, the results of Table 3 are shown by a conversion-polymerization time curve (—○—).

EXAMPLE 6

The process of Example 5 was repeated except for using 0.0112 g ($3.7 \times 10^{-5}$ mole) of 2,2'-azobis(2-methylpropionamidoxime) dihydrochloride in place of 0.0085 g ($3.7 \times 10^{-5}$ mole) of 2,2'-azobis(2-methylpropionamidoxime).

The results are shown in Table 3.

In FIG. 3, the results of Table 3 are shown by a conversion-polymerization time curve (—△—).

Comparative Example 5

The process of Example 5 was repeated except for using 0.01 g ($3.7 \times 10^{-5}$ mole) of V-50 in place of 2,2'-azobis(2-methylpropionamidoxime).

The results are shown in Table 3.

In FIG. 3, the results of Table 3 are shown by a conversion-polymerization time curve (—□—).

Comparative Example 6

The process of Example 5 was repeated except for using 0.01 g ($3.7 \times 10^{-5}$ mole) of potassium persulfate in place of 0.0085 g ($3.7 \times 10^{-5}$ mole) of 2,2'-azobis(2-methylpropionamidoxime).

The results are shown in Table 3.

In FIG. 3, the results of Table 3 are shown by a conversion-polymerization time curve (—□—).

TABLE 3

| | Polymerization time (hrs) | | | | | | | |
|---|---|---|---|---|---|---|---|---|
| | 0.5 | 1.0 | 1.5 | 2.0 | 3.0 | 4.0 | 5.0 | 6.0 |
| Example 5 | 32.5 | 50.0 | 61.5 | 69.0 | 78.3 | 84.1 | 87.6 | 89.2 |
| Example 6 | 28.9 | 47.1 | 57.6 | 66.3 | 75.2 | 82.4 | 86.8 | 88.0 |
| Comparative Example 5 | 22.4 | 40.1 | 52.0 | 59.9 | 71.2 | 77.3 | 81.1 | 83.9 |
| Comparative Example 6 | 7.7 | 16.0 | 21.6 | 27.4 | 37.4 | 46.1 | 52.5 | 59.6 |

In Table 3, values are conversion (%) per unit time.

As is clear from Table 3 and FIG. 3, acrylic acid can be polymerized effectively in a short time according to the process of the present invention compared with the cases of using V-50 and potassium persulfate as a polymerization initiator.

EXAMPLE 7

To 380 g of deionized water, 20 g of acrylamide and $3.7 \times 10^{-5}$ mole of 2,2'-azobis(2-methylpropionamidoxime) disuccinate were added and polymerized at 50° C. in a nitrogen atmosphere.

The results are shown in Table 4.

EXAMPLES 8 to 14

The process of Example 7 was repeated except for using various salts of 2,2'-azobis(2-methylpropionamidoxime) as listed in Table 4 in place of 2,2'-azobis(2-methylpropionamidoxime) disuccinate.

The results are shown in Table 4.

TABLE 4

| | | Polymerization time (hrs) | | | | | | | |
|---|---|---|---|---|---|---|---|---|---|
| Example No. | Kind of salt | 0.5 | 1.0 | 1.5 | 2.0 | 3.0 | 4.0 | 5.0 | 6.0 |
| 7 | Disuccinate | 24.8 | 48.9 | 63.5 | 70.0 | 78.9 | 83.6 | 86.1 | 89.4 |
| 8 | Dicitrate | 25.4 | 47.5 | 64.5 | 75.2 | 80.5 | 84.5 | 87.4 | 90.3 |
| 9 | Dioxalate | 26.1 | 49.1 | 64.0 | 71.3 | 82.4 | 85.9 | 89.9 | 93.6 |
| 10 | Monotartarate | 21.5 | 42.8 | 56.0 | 63.3 | 73.9 | 76.8 | 81.1 | 84.8 |
| 11 | Dimalate | 29.7 | 50.7 | 62.5 | 69.7 | 79.3 | 84.5 | 87.3 | 89.7 |
| 12 | Di-p-toluenesulfonate | 17.8 | 40.4 | 51.2 | 60.1 | 65.8 | 69.3 | 72.4 | 72.6 |
| 13 | Dimethanesulfonate | 25.6 | 46.9 | 63.7 | 72.6 | 79.1 | 83.3 | 86.4 | 88.8 |
| 14 | Diglycolate | 22.4 | 44.3 | 60.0 | 66.2 | 78.6 | 80.4 | 82.9 | 85.3 |

In Table 4, values are conversion (%) per unit time.

As is clear from the results of Table 4, acrylamide can be polymerized effectively in a short time by using various acid salts of 2,2'-azobis(2-methylpropionamidoxime).

As mentioned above, acrylic acid and water-soluble derivatives thereof can be polymerized or copolymerized effectively in a short time by using an inorganic or organic acid salt of 2,2'-azobis(2-methylpropionamidoxime) as a polymerization initiator or a mixture of 2,2'-azobis(2-methylpropionamidoxime) and an inorganic acid or organic acid. Further, according to the present invention, since an amidoxime group can be introduced into a terminal of polymer, the resulting polymer can have a function as a metal chelate.

What is claimed is:

1. A process for producing a polymer or copolymer of acrylic acid or a water-soluble derivative thereof, which comprises polymerizing acrylic acid or a water-soluble derivative thereof using as a polymerization initiator an inorganic acid salt or organic acid salt of 2,2'-azobis(2-methylpropionamidoxime).

2. A process according to claim 1, wherein acrylic acid, methacrylic acid, acrylamide or methacrylamide is polymerized.

3. A process according to claim 1, wherein the polymerization initiator is obtained by reacting 2,2'-azobis(2-methylpropionamidoxime) with an acid having a pKa of 4.25 or less at 25° C.

4. A process according to claim 1, wherein the inorganic acid is hydrochloric acid, sulfuric acid or phosphoric acid.

5. A process according to claim 1, wherein the organic acid is methanesulfonic acid, p-toluenesulfonic acid, trifluoroacetic acid, oxalic acid, succinic acid, citric acid, tartaric acid, malic acid, glycolic acid or malonic acid.

6. A process according to claim 1, wherein a mixture of 2,2'-azobis(2-methylpropionamidoxime) and an inorganic acid or an organic acid is used in place of the inorganic acid salt or organic acid salt of 2,2'-azobis(2-methylpropionamidoxime).

7. A process according to claim 6, wherein the inorganic acid is hydrochloric acid, sulfuric acid or phosphoric acid.

8. A process according to claim 6, wherein the organic acid is methanesulfonic acid, p-toluenesulfonic acid, acetic acid, trifluoroacetic acid, oxalic acid, succinic acid, citric acid, tartaric acid, malic acid, glycolic acid or malonic acid.

9. An inorganic acid salt or organic acid salt of 2,2'-azobis(2-methylpropionamidoxime) obtained by reacting 2,2'-azobis(2-methylpropionamidoxime) with an acid having a pKa of 4.25 or less at 25° C.

10. An inorganic acid salt or organic acid salt according to claim 9, wherein the inorganic acid is hydrochloric acid or the organic acid is succinic acid, citric acid, oxalic acid, tartaric acid, malic acid, p-toluenesulfonic acid, methanesulfonic acid or glycolic acid.

11. A process according to claim 1, wherein the water-soluble derivative of acrylic acid is acrylamide, methacrylamide, N-methylolacrylamide, N-methylolmethacrylamide, methacrylic acid, 2-acrylamide-2-methylpropanesulfonic acid, alkali metal salts thereof, ammonium salts thereof, dimethylaminoethyl acrylate, dimethylaminoethyl methacrylate, N,N-dimethylaminopropylacrylamide, N-N-dimethylaminopropylmethacrylamide, acid addition salts thereof or quaternary salts thereof.

* * * * *